(12) United States Patent
Agami et al.

(10) Patent No.: US 9,243,986 B2
(45) Date of Patent: Jan. 26, 2016

(54) METHOD FOR EVALUATING ABSORBENCY OF AN ABSORBENT ARTICLE

(71) Applicant: The Procter & Gamble Company, Cincinnati, OH (US)

(72) Inventors: Sion Agami, Mason, OH (US); Connie Michelle Dunaway, West Chester, OH (US); Amanda Marie Romeu, Boston, MA (US)

(73) Assignee: The Procter & Gamble Company, Cincinnati, OH (US)

( * ) Notice: Subject to any disclaimer, the term of this patent is extended or adjusted under 35 U.S.C. 154(b) by 309 days.

(21) Appl. No.: 14/053,632

(22) Filed: Oct. 15, 2013

(65) Prior Publication Data

US 2014/0102183 A1   Apr. 17, 2014

Related U.S. Application Data

(60) Provisional application No. 61/713,799, filed on Oct. 15, 2012.

(51) Int. Cl.
*G01N 5/02* (2006.01)
*A61F 13/84* (2006.01)

(52) U.S. Cl.
CPC *G01N 5/02* (2013.01); *A61F 13/84* (2013.01); *A61F 2013/8473* (2013.01); *A61F 2013/8488* (2013.01); *A61F 2013/8491* (2013.01)

(58) Field of Classification Search
CPC ............. G01N 5/02; A61F 2013/8473; A61F 2013/8488; A61F 2013/8491
See application file for complete search history.

(56) References Cited

U.S. PATENT DOCUMENTS

| | | | | |
|---|---|---|---|---|
| 3,706,222 A | * | 12/1972 | Smith | G01N 3/32 73/809 |
| 5,260,345 A | | 11/1993 | DesMarais et al. | |
| 6,623,464 B2 | | 9/2003 | Bweick-Sonntag et al. | |
| 7,402,723 B2 | | 7/2008 | Stone et al. | |
| 7,521,588 B2 | | 4/2009 | Stone et al. | |
| 7,659,372 B2 | | 2/2010 | Hood et al. | |
| 2008/0217809 A1 | * | 9/2008 | Zhao | B29C 43/222 264/229 |

* cited by examiner

*Primary Examiner* — Paul West
(74) *Attorney, Agent, or Firm* — Andrew J. Hagerty

(57) ABSTRACT

A method of evaluating the absorbency of an absorbent article comprises the steps of: (i) providing an absorbent article comprising a topsheet and having a longitudinal axis, a transverse axis, a first longitudinal end and a second longitudinal end; (ii) disposing the absorbent article in a flat configuration in a plane defined by the longitudinal axis and the transverse axis of the absorbent article; (iii) twisting the longitudinal ends in opposite directions in planes perpendicular to the longitudinal axis; (iv) twisting the longitudinal ends in directions opposite that of step (iii); (v) applying artificial bodily fluid to the topsheet of said absorbent article during steps (iii) and/or (iv); and (vi) repeating steps (iii) and (iv) after the artificial bodily fluid is applied to the topsheet.

7 Claims, 4 Drawing Sheets

METHOD FOR EVALUATING ABSORBENCY OF AN ABSORBENT ARTICLE

FIELD OF THE INVENTION

The present invention relates to a method for evaluating the absorbency of an absorbent article, in particular evaluating the absorbency of a feminine hygiene article while the longitudinal ends of the article are twisted in opposite directions.

BACKGROUND OF THE INVENTION

Absorbent articles, such as feminine hygiene articles, are important for consumers. In particular, comfort and protection against leaks are important benefits, especially for people who lead active lifestyles. Absorbent articles are therefore subject to many stresses during wear. Several factors can impact a consumer's perception of comfort and protection against leaks, such as flexibility of the article during wear, ability of the article to adapt to her movements during wear, and the ability of the article to absorb bodily fluids encountered in stress conditions during wear.

It is therefore desired to develop a method for evaluating the absorbency of an absorbent article under conditions that simulate the twisting that the article undergoes during wear and during which time the absorbent article absorbs bodily fluids.

SUMMARY OF THE INVENTION

A method of evaluating the absorbency of an absorbent article comprises the steps of: (i) providing an absorbent article comprising a topsheet and having a longitudinal axis, a transverse axis, a first longitudinal end and a second longitudinal end; (ii) disposing the absorbent article in a flat configuration in a plane defined by the longitudinal axis and the transverse axis of the absorbent article; (iii) twisting the first longitudinal end of said article in a clockwise or counterclockwise direction in a plane perpendicular to the longitudinal axis of the article and simultaneously twisting the second longitudinal end of said article in a direction opposite of the first longitudinal end in a plane perpendicular to the longitudinal axis of the article; (iv) twisting the first longitudinal end in a direction opposite that of step (iii) and simultaneously twisting the second longitudinal end in a direction opposite that of step (iii); (v) applying artificial bodily fluid to the topsheet of said absorbent article during steps (iii) and/or (iv); and (vi) repeating steps (iii) and (iv) after said artificial bodily fluid is applied to said topsheet.

The method of the present invention enables evaluation of the flow of the artificial bodily fluid on and into the absorbent article under conditions which simulate the twisting that the article undergoes during wear. The method can further additional steps that enable the evaluation of the amount of artificial bodily fluid absorbed by the article relative to the amount that "runs-off" or is otherwise not absorbed by the article, in order to evaluate the ability of the article to prevent leaks during wear. The method therefore provides a dynamic evaluation of absorbency as compared to conventional static test methods.

DETAILED DESCRIPTION OF THE INVENTION

As used herein, the term "absorbent article" refers to devices that absorb and contain body exudates, primarily menses and/or urine. The term "disposable" is used herein to describe absorbent articles which are not intended to be laundered, or otherwise restored or reused as an absorbent article after a single use. Examples of absorbent articles include feminine hygiene garments such as sanitary napkins, pantiliners, interlabial devices, hemorrhoid pads, adult incontinence articles, wipes, tampons, and the like.

Disposable absorbent articles and components thereof, including the topsheet, backsheet, absorbent core, and any individual layers of these components, have a body surface and a garment surface. As used herein, "body surface" means that surface of the article or component which is intended, to be worn toward or adjacent to the body of the wearer, while the "garment surface" is on the opposite side and is intended to be worn toward or placed adjacent to the wearer's undergarments when the disposable absorbent article is worn.

In general, the method of the present invention for evaluating the absorbency of an absorbent article comprises the steps of: (i) providing an absorbent article comprising a topsheet and having a longitudinal axis, a transverse axis, a first longitudinal end and a second longitudinal end; (ii) disposing the absorbent article in a flat configuration in a plane defined by the longitudinal axis and the transverse axis of the absorbent article; (iii) twisting the longitudinal ends in opposite directions in planes perpendicular to the longitudinal axis; (iv) twisting the longitudinal ends in directions opposite that of step (iii); (v) applying artificial bodily fluid to the topsheet of said absorbent article during steps (iii) and/or (iv); and (vi) repeating steps (iii) and (iv) after the artificial bodily fluid is applied to the topsheet.

Figure 1A:
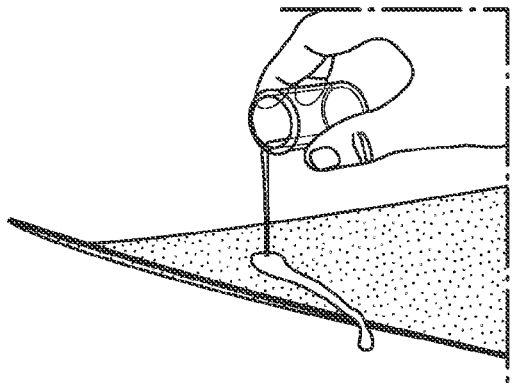
FIGS. 1A-1B are perspective views of a method for evaluating the comparative absorbency of two different absorbent articles.
Figure 1B:
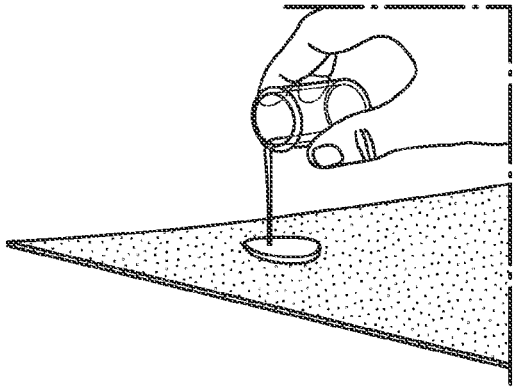

The methods herein can be implemented to provide a qualitative evaluation or a quantitative evaluation of absorbency. A method providing a qualitative evaluation can utilize, e.g., manual twisting of the longitudinal ends of the article by hand while dispensing artificial bodily fluid onto the topsheet of the article in an amount that is not necessarily quantified. In this aspect, the flow of the artificial bodily fluid on and into the absorbent article can be evaluated to provide a qualitative evaluation of the absorbency. For example, it can be observed whether the artificial bodily fluid "runs-off" the topsheet as shown in FIG. 1A, or does not "run-off" the topsheet as shown in FIG. 1B. It is preferred, especially for a qualitative evaluation, to utilize an artificial bodily fluid that is colored so as to more readily be seen when applied to the article, as shown in FIGS. 1A and 1B.

Such qualitative evaluations can also be used to produce images or videos that can be utilized in presentations or product advertising copy.

The method of the present invention can comprise additional steps to provide a quantitative evaluation of the amount of artificial bodily fluid absorbed by the absorbent article. Such a method can utilize an apparatus as described herein while applying a known amount of artificial bodily fluid to the article and measuring the amount absorbed while the longitudinal ends of the article are twisted back and forth by the apparatus. Such a method may generally further comprise one or more of the following additional steps:

provind an apparatus comprising a first clamp and a second clamp; the apparatus can further comprise one or more of the following elements: a rotary power source of manual, mechanical, electrical, or electronic origin, a gear mechanism designed to transfer the rotary motion from the rotary power source to both sides of a clamping stand, two cam elements, one at either end of the clamping stand wherein the cam elements are designed to transform the rotary motion from the rotary power source into an oscillating motion and wherein the oscillating motion of the second cam is 180 degrees out of phase with the oscillating motion of the first cam, a first clamp in mechanical connection to the first cam and a second clamp in mechanical connection to the second cam wherein clamps are mechanically connected to the cams in a manner so that the distance between the clamps can be adjusted via the sliding of one or both clamps along an axial line formed between the centerpoints of the two clamps, the two clamps are also spaced apart so that an average length feminine hygiene pad can be attached between the two clamps, optionally, a dispensing rack positioned above the test stand, optionally, an adjustable syringe pump attached to the dispensing rack such that the output of the syringe pump dispenses fluid above the center point of a feminine hygiene pad, optionally, a control system for the syringe pump that controls both the volume dispensed and the dispensing rate of fluid from the syringe pump, and optionally, a still or video image recording system focused on the feminine hygiene pad so that each test run of the apparatus can be recorded for further assessments of the performance of feminine hygiene products;

weighing the absorbent article before clamping the longitudinal ends of the article in the clamps of the apparatus;

clamping the first longitudinal end of the article in the first clamp and clamping the second longitudinal end of the article in the second clamp;

activating the apparatus to twist the longitudinal ends of said absorbent article;

applying a known amount of the artificial bodily fluid to the article after activating the apparatus;

stopping the apparatus;

removing the longitudinal ends from the clamps;

weighing the absorbent article after removing from the clamps; and calculating the amount of fluid, absorbed by the article.

Figure 2A:
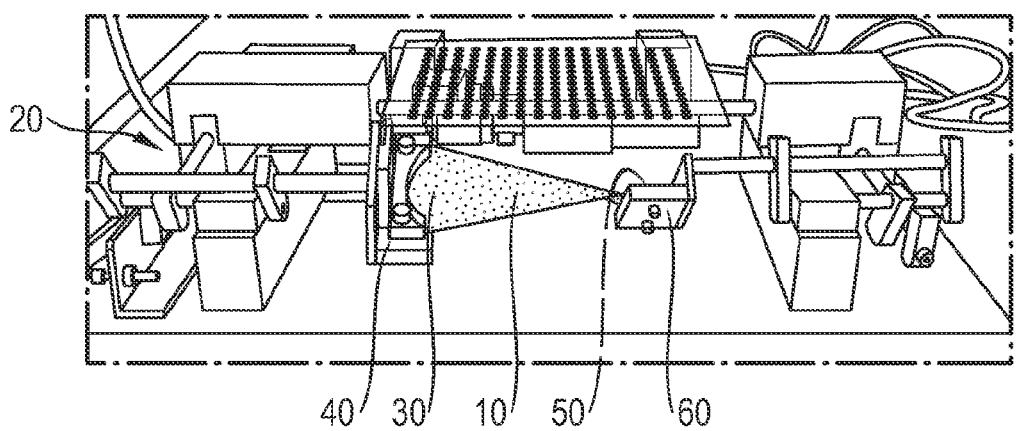
FIGS. 2A-2C are perspective views of a method for evaluating absorbency of an absorbent article.
Figure 2B:
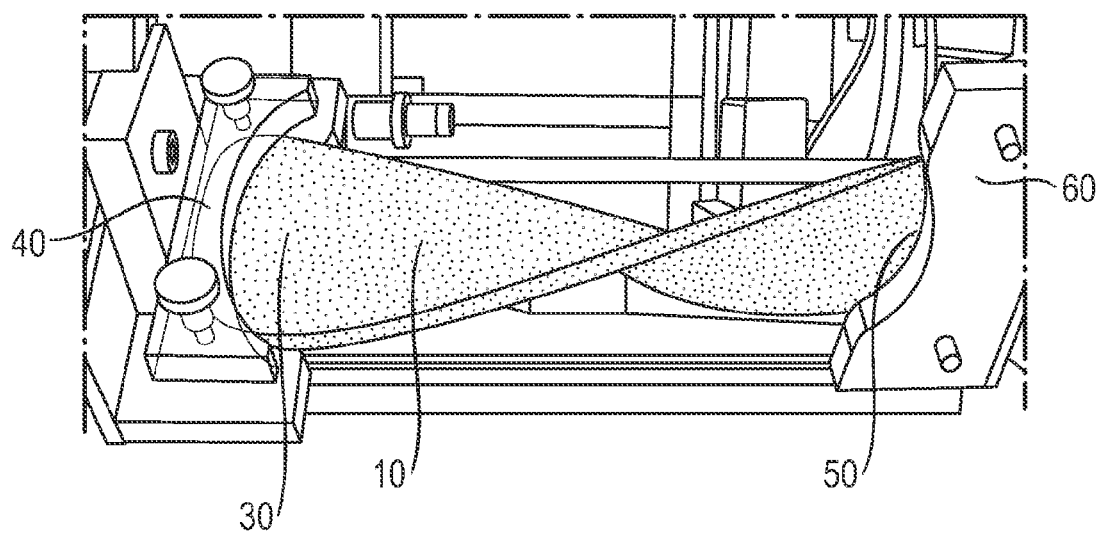
Figure 2C:
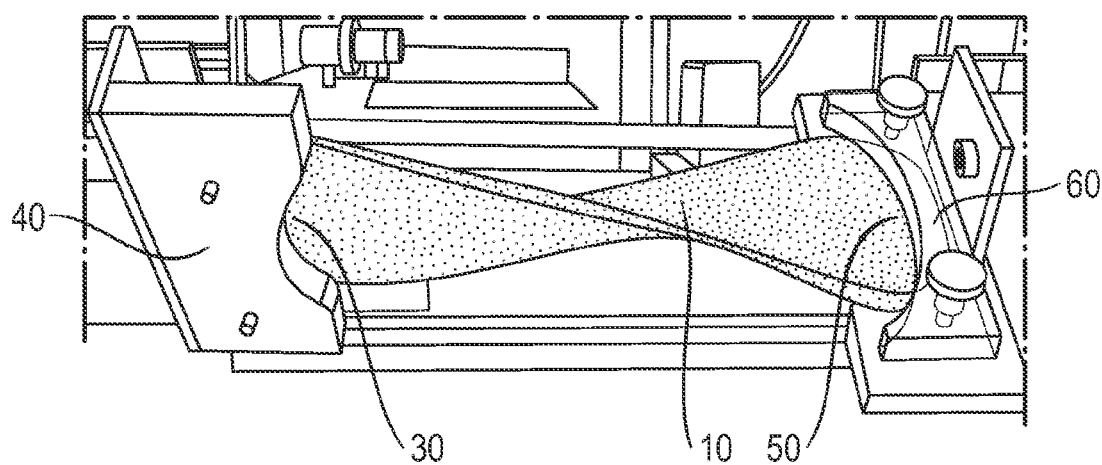

FIGS. 2A, 2B and 2C illustrate a method of evaluating the absorbency of an absorbent article 10 utilizing an apparatus 20 as described herein. The absorbent article 10 is a sanitary napkin. The absorbent article 10 is disposed in a flat configuration in a plane defined by the longitudinal axis and transverse axis of the absorbent article 10 and clamped to the apparatus 20. The first longitudinal end 30 of the absorbent article 10 is placed in a first clamp 40 of the apparatus 20 and the second longitudinal end 50 of the absorbent article 20 is placed in a second clamp 60 of the apparatus 20. The apparatus 20 is then activated such that the first longitudinal end 30 is twisted by rotation of the first clamp 40 in a clockwise direction and the second longitudinal end 50 is twisted by rotation of the second clamp 60 in a counterclockwise direction, as shown in FIGS. 2A and 2B. The apparatus 20 then twists the longitudinal ends 30, 50 in opposite directions by rotation of the first clamp 40 in a counterclockwise direction and rotation of the second clamp 60 in a clockwise direction, as shown in FIG. 2C. The apparatus 20 then continues to twist the longitudinal ends 30, 50 of the article 10 back-and-forth in opposite directions in an oscillating manner. During this continuous, back-and-forth twisting of the longitudinal ends 30, 50, the artificial bodily fluid is applied to the topsheet of the absorbent article 10, preferably in the center of the topsheet.

The longitudinal ends of the absorbent article are generally twisted by rotating the clamps of the apparatus in an oscillating manner within a range of +45 to −45 degrees with respect to the plane defined by the longitudinal axis and transverse axis of the absorbent article in its original Out configuration before twisting (i.e. with the clamps at an angle of 0 degrees relative to the surface on which the apparatus is disposed). The resulting full range of motion provided by rotation of the clamps of the apparatus is about 90 degrees.

FIGS. 2B and 2C illustrate the oscillating, twisting motion that the pad undergoes after the apparatus is activated. In FIG. 2B, the first longitudinal end of the absorbent article is twisted −45 degrees and the second longitudinal end of the absorbent article is twisted +45 degrees, with respect to the plane defined by the longitudinal axis and transverse axis of the absorbent article In FIG. 2C, the first longitudinal end of the absorbent article is twisted +40 degrees and the second longitudinal end of the absorbent article is twisted −38 degrees, with respect to the plane defined by the longitudinal axis and transverse axis of the absorbent article.

The speed of twisting the longitudinal ends through one full cycle (one back-and-forth motion or one full oscillation of the clamps of the apparatus) is generally within with range of from about 0.4 second to about 25 seconds, preferably from about 1 second to about 5 seconds, and more preferably about 1.8 seconds.

It is recognized that the apparatus can be adjusted to alter the angle of twisting and speed of twisting in order to simulate different movements that the absorbent article may undergo during wear by a consumer of the absorbent article.

Absorbent Article

In general, the absorbent article evaluated in the method of the present invention will comprise a topsheet. The top outer surface of the absorbent article will typically comprise the topsheet material and the bottom outer surface will typically comprise a backsheet material. An absorbent core material will typically be disposed in between the topsheet material and the backsheet material. Therefore, an absorbent article can comprise a topsheet material, a backsheet material, and an absorbent core material disposed therebetween.

The backsheet and the topsheet typically comprise the outer surface(s) of the absorbent article and are positioned adjacent the garment surface and the body surface, respectively, of the absorbent core. The absorbent core can be joined with the topsheet, the backsheet, or both in any manner as is known by attachment means such as those well known in the art. However, embodiments of the present invention are envisioned wherein portions of the entire absorbent core are unattached to either the topsheet, the backsheet, or both.

Figure 3:
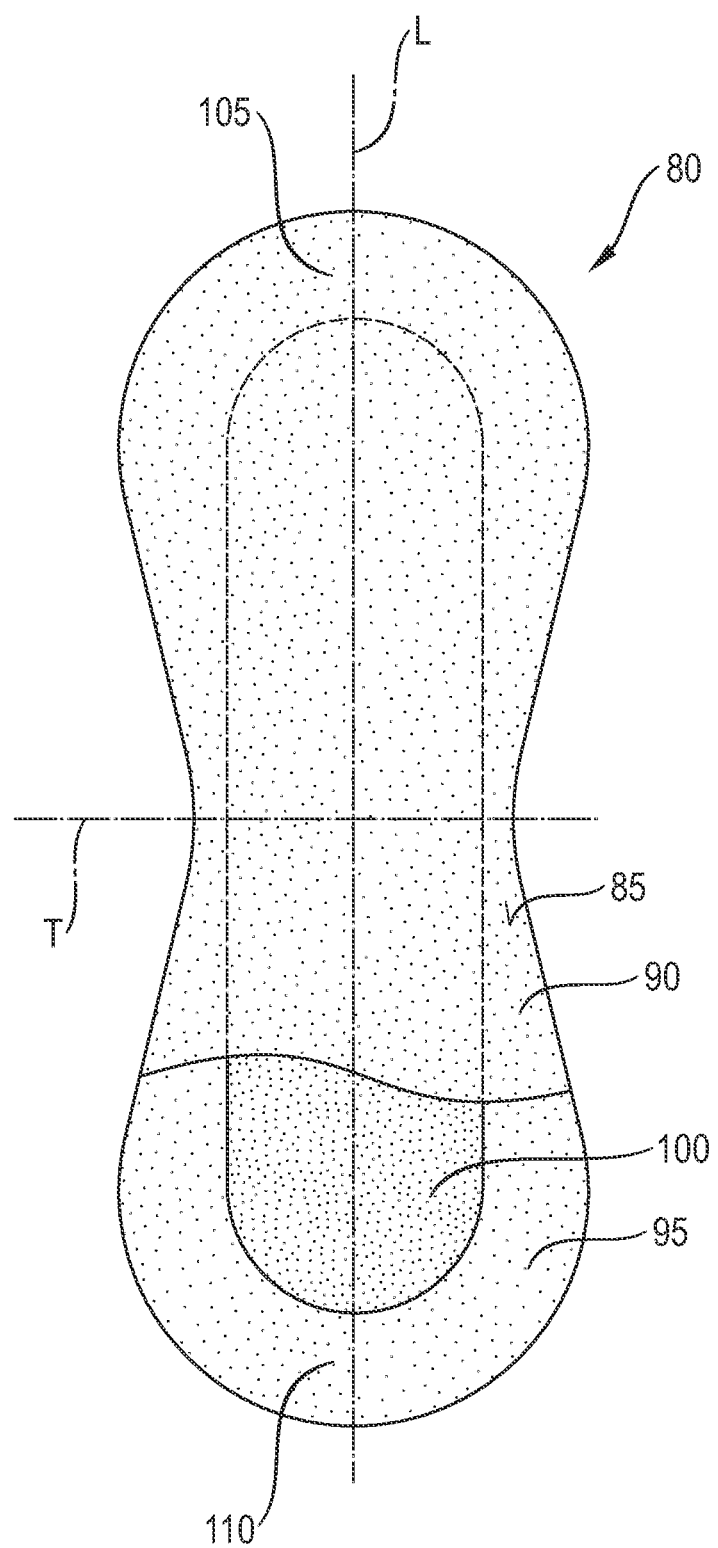
FIG. 3 is a top view of an absorbent article comprising a topsheet, backsheet, and an absorbent core.

FIG. 3 shows an absorbent article 80, that can be a sanitary napkin or pantiliner, having a body facing surface 85 comprising a topsheet 90, a liquid impervious backsheet 95 joined to the topsheet 90, an absorbent core 100. The absorbent article 80 has a longitudinal axis L and a transverse axis T, and a first longitudinal end 105 and a second longitudinal end 110. The absorbent article 80 may also be provided with additional features commonly found in napkins, including "wings" or "flaps" (not shown) as is known in the art and/or a fluid acquisition layer(s) to promote fluid transport to the absorbent core 100. Likewise, the topsheet of the absorbent article can have various optional characteristics, as is known in the art. For example, the topsheet 90 can have channels embossed therein to direct fluid flow, and can have apertures therethrough to aid in fluid acquisition.

The topsheet is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

Suitable topsheet materials are described in detail in, e.g., U.S. Pat. Nos. 7,402,723 or 7,521,588.

The backsheet is typically impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. The backsheet can, for instance, be a breathable backsheet such as that described in U.S. Pat. No. 6,623,464.

Apparatus for Twisting an Absorbent Article

Although the longitudinal ends of the absorbent article can be twisted manually by hand as previously described, it can be preferred to utilize an apparatus designed to more precisely twist the longitudinal ends of the absorbent article, especially if a more quantitative evaluation of absorbency is desired.

Figure 4:
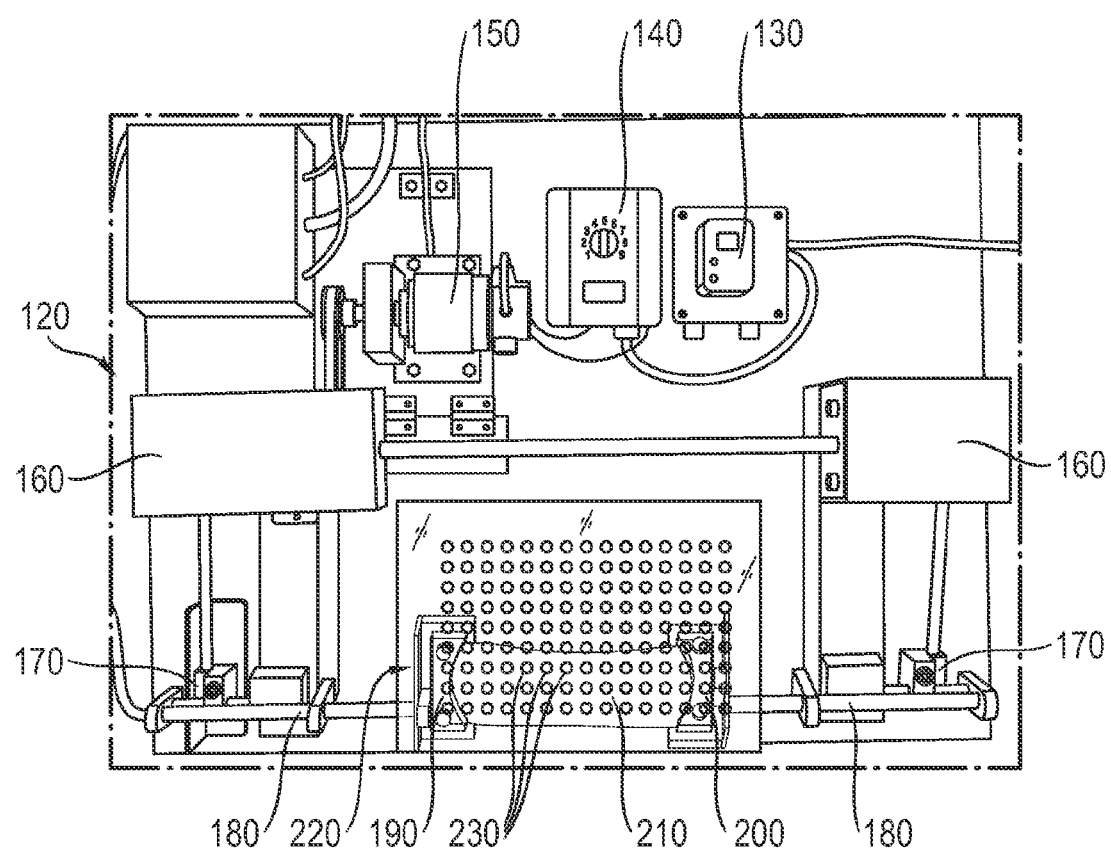
FIG. 4 is a top view of an apparatus used in a method for evaluating the absorbency of an absorbent article.

FIG. 4 illustrates an apparatus 120 that can he utilized in the method of the present invention. The system has an on-off switch box 130, commonly found in hardware or electronics supply stores. The switch box can optionally be fitted with a timer, counter, or other functionality which would enhance the capabilities of the apparatus. The power is transferred from the on-off switch box 130 to a variable DC voltage supply system 140. A suitable power supply 140 is a Dayton Electric variable DC voltage power supply, model 4Z527E, available from W.W. Grainger Inc., Niles Ill., USA.

The variable DC voltage power supply 140 is used to control the rotational speed of a variable speed DC motor 150. A suitable motor 150 is a Dayton Electric motor, model 1LPW5, also available from W. W. Grainger Inc., Niles Ill., USA. The voltage power supply 140 for the motor 150 can be adjusted to generate 23 twisting cycles/minute.

The drive shaft of the variable speed motor 150 is connected to the test apparatus 120 via a gear drive pulley and belt system 160. A suitable gear drive pulley is a Browning 28XLB037 aluminum pulley, 2 inches in diameter, available from W.W. Grainger Inc., Niles Ill., USA. An identical receiving pulley is mounted on the apparatus transfer drive shaft, which is a 24 inch long, ½ inch aluminum shaft. Appropriate support bearings for the apparatus transfer shaft are mounted about 6 inches from either end of the shaft. At each end of the apparatus transfer drive shaft are off-set cam push-rod systems 170 designed to convert the rotary motion of the drive shaft into back-and-forth linear motion perpendicular to the shaft. The cams at the two ends of the apparatus transfer shaft of the off-set cam and push-rod systems 170 are off-set from each other by 180 degrees, so that while one rod is pushing at one end, the other rod is pulling back in towards the drive shaft. The stroke distance of these push-rods are 1.25 inches and the overall length of the push rods are 10 inches.

The ends of the push-rods are connected to a second pair of off-set cam pivot systems 180, which allows transfer of the linear push-rod motion into an arching or twisting motion of a first clamp 190 and a second clamp 200. The second pair of off-set cam pivot systems 180 are set up to transfer the 1.25 inch push-rod stroke into an approximate 90 degree rotational movement on the shafts of the first and second clamps 190, 200. Due to the off-set of the cam system 170 mentioned previously, the twisting motion of the first and second clamps 190, 200 are 180 degrees out of phase with each other, creating a twisting motion within the absorbent article 210. The center line of the absorbent article 210 in the first and second clamps 190, 200 is along the center axis of the twisting motion, so that the centerline of the absorbent article 210 does not change during the method. The first and second clamps 190, 200 of the product clamping system are designed so that they can be moved along the shaft of the product clamping system so that absorbent articles 210 of different length can be accommodated by the test stand apparatus 120.

A clear polycarbonate sheet 220 of plastic is mounted horizontally above the first and second clamps 190, 200. This polycarbonate sheet 220 is 8×12×¼ inches (20.32 cm×30.48 cm×0.635 cm), and has a set of ¼ inch (0.635 cm) holes 230 drilled through it Wherein the holes are in a grid pattern 11⁄16 inches (1.75 cm) from each other. This set of holes 230 above the absorbent article 210 being tested is a horizontal dispensing grid and is used to reproducibly drop artificial bodily fluids onto a series of absorbent articles 210 at approximately the same location on the absorbent article 210 each time fluid is dispensed. The bottom of the dispensing grid sheet 220 is approximately 3.5 inches from the top of the absorbent article 210 being tested. These holes 230 are used for placement of either manual syringes or automatic dispensing syringe outlet tips, such as with the Hamilton Microlab 600 Series automatic dispensing syringe pump, available from Hamilton Company USA, Reno Nev., USA. The various holes 230 allow placement of the fluid onto the absorbent article 210 at reproducible points on the absorbent article 210, assuring consistent fluid delivery locations and rates to the absorbent article 210 being tested.

Artificial Bodily Fluid

The method of the present invention comprises applying an artificial bodily fluid utilized in the method of the present invention can be, for example, an artificial urine fluid or artificial menstrual fluid. Suitable artificial urine fluids are described in, e.g., U.S. Pat. No. 5,260,345 (col. 27, lines 34-54). Suitable artificial menstrual fluids are described in, e.g., U.S. Pat. No. 7,659,372.

In the methods of the present invention, the amount of artificial bodily fluid applied to the topsheet of the absorbent article generally ranges from about 1 milliliter to about 5 milliliter, preferably from about 1 milliliter to about 3 milliliter.

The artificial bodily fluid can be applied to various parts of the topsheet of the absorbent article, depending upon the areas of the absorbent article to be evaluated for absorbency.

Preferably, the artificial bodily fluid is applied to the center of the topsheet of the absorbent article. However, the artificial bodily fluid can be added to areas of the topsheet of the absorbent article other than the center in order to evaluate absorbency of the absorbent article within a given area of the topsheet. This can be preferred when the topsheet comprises more than one material and/or more than one texture on the surface of the outer surface of the topsheet.

Since many topsheet materials for absorbent articles are essentially white or non-colored, the artificial bodily fluid utilized in the methods herein is preferably colored such that it is easily visible when applied to the absorbent article being evaluated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can he made without departing from the spirit and scope of the invention. It is therefore intended to cover in the appended claims all such changes and modifications that are within the scope of this invention.

What is claimed is:

1. A method for evaluating absorbency of an absorbent article, said method comprising the steps of:
   (i) providing an apparatus comprising a first clamp and a second clamp;
   (ii) providing an absorbent article comprising a topsheet and having a longitudinal axis, a transverse axis, a first longitudinal end and a second longitudinal end;
   (iii) weighing the absorbent article a first time;
   (iv) disposing the absorbent article in a flat configuration in a plane defined by the longitudinal axis and the transverse axis of the absorbent article;
   (v) clamping the first longitudinal end of the article in the first clamp and clamping the second longitudinal end of the article in the second clamp;
   (vi) activating the apparatus thereby twisting the first longitudinal end of said article in a clockwise or counterclockwise direction in a plane perpendicular to the longitudinal axis of the article and simultaneously twisting the second longitudinal end of said article in a direction opposite of the first longitudinal end in a plane perpendicular to the longitudinal axis of the article;
   (vii) twisting the first longitudinal end in a direction opposite that of step
   (vi) and simultaneously twisting the second longitudinal end in a direction opposite that of step (vi);
   (viii) applying artificial bodily fluid to the topsheet of said absorbent article during steps (vi) and/or (vii);
   (ix) repeating steps (vi) and (vii) after said artificial bodily fluid is applied to said topsheet;
   (x) stopping the apparatus;
   (xi) removing the longitudinal ends from the clamps;
   (xii) weighing the absorbent article a second time; and
   (xiii) calculating the amount of fluid absorbed by the article using values from steps (iii) and (xii).

2. The method of claim 1, wherein the absorbent article is a feminine hygiene article.

3. The method of claim 1, wherein the artificial bodily fluid is artificial menstrual fluid.

4. The method of claim 1, wherein the amount of fluid applied to the article is from about 1 milliliter to about 5 milliliters.

5. The method of claim 1, wherein the fluid is applied to the center of the topsheet of the article.

6. The method of claim 1, wherein the fluid is colored.

7. The method of claim 1, wherein each longitudinal end is twisted within a range of about +45 degrees to about −45 degrees with respect to the plane defined by the longitudinal axis and the transverse axis of the article.

* * * * *